(12) United States Patent
Aristovich et al.

(10) Patent No.: US 11,589,827 B2
(45) Date of Patent: Feb. 28, 2023

(54) NERVE ACTIVITY MONITORING

(71) Applicants: GALVANI BIOELECTRONICS LIMITED, Brentford (GB); UCL BUSINESS LTD, London (GB)

(72) Inventors: Kirill Aristovich, Greater London (GB); David Holder, Greater London (GB); Daniel Chew, Brentford (GB); Matteo Donega, Brentford (GB)

(73) Assignees: UCL Business PLC, London (GB); Galvani Bioelectronics Limited, Brentford (GB)

( * ) Notice: Subject to any disclaimer, the term of this patent is extended or adjusted under 35 U.S.C. 154(b) by 229 days.

(21) Appl. No.: 16/622,675

(22) PCT Filed: Jun. 22, 2018

(86) PCT No.: PCT/GB2018/051750
§ 371 (c)(1),
(2) Date: Dec. 13, 2019

(87) PCT Pub. No.: WO2018/234825
PCT Pub. Date: Dec. 27, 2018

(65) Prior Publication Data
US 2021/0137463 A1 May 13, 2021

(30) Foreign Application Priority Data
Jun. 22, 2017 (GB) .................... 1709997

(51) Int. Cl.
*A61B 5/00* (2006.01)
*G16H 20/30* (2018.01)
(Continued)

(52) U.S. Cl.
CPC .......... *A61B 5/7246* (2013.01); *A61B 5/1118* (2013.01); *A61B 5/4029* (2013.01);
(Continued)

(58) Field of Classification Search
CPC .......... A61B 2560/0475; A61B 5/0031; A61B 5/021; A61B 5/02116; A61B 5/024;
(Continued)

(56) References Cited

U.S. PATENT DOCUMENTS

| 2011/0071421 A1 | 3/2011 | Gozani et al. |
| 2012/0029600 A1 * | 2/2012 | Zhou .................. A61B 5/24 |
| | | 607/62 |

(Continued)

FOREIGN PATENT DOCUMENTS

| WO | WO-2010031406 A1 | 3/2010 |
| WO | WO-2016170327 A1 | 10/2016 |

OTHER PUBLICATIONS

Anonymous., "Proceedings of the 18th International Conference on Biomedical Applications of Electrical Impedance Tomography| Zenodo", XP055535000, Jun. 21, 2017, Retrieved from the Internet URL: https://zenodo.org/record/892679#.Yfl0xepBxPZ, retrieved on Dec. 14, 2018, 94 pages.

(Continued)

*Primary Examiner* — George Manuel
(74) *Attorney, Agent, or Firm* — Merchant & Gould P.C.

(57) ABSTRACT

There is provided a nerve activity monitoring method that includes receiving an input signal indicative of activity in a nerve of a subject; receiving physiological data indicative of physiological activity in the subject; establishing a relationship between the physiological data and the input signal;

(Continued)

identifying a plurality of periodic portions in the input signal based on the relationship between the physiological data and the input signal; and outputting the periodic portions identified.

14 Claims, 10 Drawing Sheets

(51) Int. Cl.
*G16H 40/67* (2018.01)
*G16H 50/20* (2018.01)
*A61B 5/11* (2006.01)
*A61N 1/36* (2006.01)
*A61B 5/388* (2021.01)
*A61N 1/05* (2006.01)

(52) U.S. Cl.
CPC .......... *A61B 5/686* (2013.01); *A61B 5/7228* (2013.01); *A61B 5/742* (2013.01); *A61N 1/36139* (2013.01); *G16H 20/30* (2018.01); *G16H 40/67* (2018.01); *G16H 50/20* (2018.01); *A61B 5/388* (2021.01); *A61B 2560/0475* (2013.01); *A61N 1/0556* (2013.01)

(58) Field of Classification Search
CPC ....... A61B 5/0536; A61B 5/1118; A61B 5/24; A61B 5/318; A61B 5/349; A61B 5/352; A61B 5/388; A61B 5/4029; A61B 5/6847; A61B 5/686; A61B 5/6877; A61B 5/7203; A61B 5/7228; A61B 5/7246; A61B 5/7282; A61B 5/742; A61N 1/0556; A61N 1/36139; G16H 20/30; G16H 40/67; G16H 50/20
See application file for complete search history.

(56) References Cited

U.S. PATENT DOCUMENTS

2014/0330404 A1    11/2014  Abdelghani et al.
2015/0142082 A1*   5/2015   Simon ............... A61N 1/36132
                                                    607/61

OTHER PUBLICATIONS

Aristovich K., et al., "Proceedings of the 18th International Conference on Biomedical Applications of Electrical Impedance Tomography," Inverse Problems, GBISSN: 0266-5611, XP055535007, figures 1-2, DOI: 10.5281/zenodo.601555, vol. 18, Jun. 21, 2017, 94 pages.
International Preliminary Report on Patentability for Application No. PCT/GB2018/051750 dated Jan. 2, 2020, 15 pages.
International Search Report and Written Opinion for Application No. PCT/GB2018/051750 dated Jan. 21, 2019, 19 pages.

* cited by examiner

NERVE ACTIVITY MONITORING

PRIORITY CLAIM

The present application is a National Phase entry of PCT Application No. PCT/GB2018/051750, filed Jun. 22, 2018, which claims priority from GB Patent Application No. 1709997.9, filed Jun. 22, 2017, which is hereby fully incorporated herein by reference.

TECHNICAL FIELD

This disclosure relates to a system, a method and a computer program for monitoring nerve activity in a more accurate manner.

BACKGROUND

Fast Neural Electrical Impedance Tomography (EIT) is a known method for producing tomographic 3D images of neuronal function. This technique was originally developed for the 10 brain where the resolution is ~1 milliseconds and 200 µm. Typically, EIT uses ~2-6 kHz and 16-60 electrodes.

In EIT an impedance signal is demodulated around a carrier with bandwidth ~1 kHz. This demodulated signal is reconstructed into images. In order for the images to be generated, it is necessary for the impedance signal to vary over time. The basis of the EIT signals (dZ)

15 relates to action potentials in a nerve. These last a few milliseconds and so have a principal frequency of ~2 kHz. When EIT is applied to neural functions, the signal-to-noise ratio (SNR) is low. Therefore, it is desirable to use averaging to enhance the SNR.

In the past, an externally evoked response in the brain or compound action potential in the nerve would be initiated for averaging signals. Typically, this average would be generated from ~128 evoked responses over ~30 seconds at 5 Hz.

Typically, the nerve activity collection apparatus might contain 16 electrodes, and one averaged data set would be produced with current injection using an opposing pair of electrodes. Then, voltage would be recorded at the remaining 14 electrodes. Next, this process would be repeated for all 16 pairs. This process would yield 16×14 transfer impedance recordings, which could be reconstructed into images.

It is desirable to image spontaneous activity in peripheral nerves, such as somatic nerves and autonomic nerves. However, this is particularly complex for autonomic nerves, since activity may be spontaneous and phasic with variable cycling, and an 'artificial' trigger such as the externally evoked response may not be present.

In addition, it is desirable to be able to detect and monitor the activity of nerves in a human or an animal subject in an accurate and reliable manner. WO 2016/170327 describes one example of a device that can be used for monitoring the activity of nerves.

Referring to FIG. 1, it is known that a peripheral nerve 10 of a human or an animal subject can be coupled to a nerve monitoring device 20 for detecting activity in nerves. This device is described in greater detail in WO 2016/170327.

The device 20 comprises a cuff 22 which wraps around an outside perimeter of the nerve 10 and is provided with a plurality of electrodes for contacting the nerve. The cuff 22 may be held in place by an elastomeric tube 18. The device 20 also comprises an associated control unit 30 coupled to and located proximal to the cuff 22.

The apparatus described in WO 2016/170327 and illustrated in FIG. 1 can be used to detect electrical activity within a nerve, using techniques such as electrical impedance tomography (EIT). These techniques can be used to generate a signal indicative of electrical activity in the nerve.

Referring to FIG. 2, the device 20 can be connected to a nerve in a human or an animal subject. In this example, the subject is a sheep 40, and the device 20 generates an EIT signal 50 indicative of the electrical activity in the vagus nerve of the sheep 40.

In addition to the detection and monitoring of the activity of nerves, it is desirable to be able to monitor physiological activity occurring in a subject and to be able to correlate nerve activity with physiological activity. This would make it possible to associate certain types of nerve activity with specific physiological responses. This may allow, for instance, medical diagnoses to be made from the detection of nerve activity. Furthermore, this may allow previously recorded nerve activity to be stimulated in a nerve in order to induce a corresponding physiological response.

Previously, it has been possible to monitor activity in the somatic nerves. These nerves are generally associated with a subject's voluntary control of their body movements. It has been possible to associate somatic nerve activity with physiological responses in a subject, such as the movement of an arm or a leg of the subject. Thus, it is possible to monitor the activity in a particular somatic nerve whilst a specific physiological response is invoked. Since somatic nerves are, in general, associated with a limited number of physiological responses, it is possible to associate somatic neve activity with its corresponding physiological response. However, the situation is more complex when monitoring autonomic nerves, which are associated with the involuntary control of internal organs.

Typically, autonomic nerves are made up of a bundle of nerve fibers, and each one of these nerve fibers may be associated with a different physiological activity. Also, the nerve activity in each fiber is likely to be continuous, so that functions such as the beating of the heart can be maintained, but can be discontinuous or variable, to allow modulation of organ physiology, and in some cases is indicative of a disease state. These characteristics of autonomic nerves make it particularly difficult to associate physiological responses with nerve activity, particularly when nerve activity is measured using techniques such as EIT.

Typically nerve activity signals are contaminated with the noise, associated with the measurement systems and environment. Commonly, the noise has a larger amplitude than the measured neural activity itself. This requires averaging of the signal which in case of autonomic spontaneous activity is not possible using conventional techniques due to signal cancellation, as will be described in detail below.

Therefore, there exists a need for a way in which to more accurately monitor nerve activity.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one aspect of the disclosure there is provided a nerve activity monitoring method comprising: receiving an input signal indicative of activity in a nerve of a subject; receiving physiological data indicative of physiological activity in the subject; establishing a relationship between the physiological data and the input signal; identifying a plurality of periodic portions in the input signal based on the relationship between the physiological data and the input signal; and outputting the periodic portions identified.

In another aspect of the disclosure there is provided a nerve activity monitoring system comprising: a communication interface arranged to receive an input signal indicative of activity in a nerve of a subject and arranged to receive physiological data indicative of physiological activity in the subject; an output module arranged to: establish a relationship between the physiological data and the input signal; identify a plurality of periodic portions in the input signal based on the relationship between the physiological data and the input signal; and output the periodic portions identified.

In another aspect of the disclosure there is provided a computer program comprising code portions which when loaded and run on a computer cause the computer to: receive an input signal indicative of activity in a nerve of a subject; receive physiological data indicative of physiological activity in the subject; establish a relationship between the physiological data and the input signal; identify a plurality of periodic portions in the input signal based on the relationship between the physiological data and the input signal; and output the periodic portions identified.

In another aspect of the disclosure there is provided a nerve activity monitoring method comprising: calculating a frequency spectrum of at least a portion of an input signal indicative of activity in a nerve of a subject; identifying a demodulation frequency within the frequency spectrum; demodulating at least two periodic portions of the input signal based on the demodulation frequency, to generate at least two demodulated signal portions; averaging the at least two demodulated signal portions, to generate an averaged signal.

In another aspect of the disclosure there is provided nerve activity monitoring system comprising: calculating a frequency spectrum of at least a portion of an input signal indicative of activity in a nerve of a subject; identifying a demodulation frequency within the frequency spectrum; demodulating at least two periodic portions of the input signal based on the demodulation frequency, to generate at least two demodulated signal portions; averaging the at least two demodulated signal portions, to generate an averaged signal.

In another aspect of the disclosure there is provided a computer program comprising code portions which when loaded and run on a computer cause the computer to: calculate a frequency spectrum of at least a portion of an input signal indicative of activity in a nerve of a subject; identify a demodulation frequency within the frequency spectrum; demodulate at least two periodic portions of the input signal based on the demodulation frequency, to generate at least two demodulated signal portions; average the at least two demodulated signal portions, to generate an averaged signal.

In another aspect of the disclosure there is provided an implantable device comprising a system as described herein.

In another aspect of the disclosure there is provided a computer-readable having stored thereon a computer program as described herein.

BRIEF DESCRIPTION OF THE DRAWINGS

Embodiments of the disclosure will be described, by way of example, with reference to the following drawings, in which.

DETAILED DESCRIPTION

Described herein is a method, a system and a computer program in which periodic portions of an input signal indicative of electrical activity of a nerve are identified. The periodic portions of the input signal are determined based on a relationship between the input signal and physiological data indicative of physiological activity in a subject. This makes it possible to identify periodic portions in the input signal, which may have otherwise been disguised due to the presence of noise. The physiological activity can be in reference to health or disease states of a subject. In addition, the relationship may be a causal and/or predictive relationship between the physiological data and the input signal.

In one aspect a 'trigger' from a measure of cyclical endogenous activity, such as an ECG reading, or a response which can be explicitly independently recorded is obtained. This 'trigger' is linked with an input signal indicative of nerve activity. In another aspect, the 'trigger' may be cyclical but it may not be possible record this 'trigger' independently. This is the case, for example, in peristalsis in the bowel. In this example, autocorrelation of the input signal could be used to identify cyclical, or 'periodic' nerve activity.

In one instance, generating an average of the periodic activity may lead to an average of zero or a diminished average. This may be due to phase cancellation of the 2 kHz action potential components, since there is no longer an artificially synced external trigger. Therefore, a method is proposed herein that generates an average that does not diminish due to cancellation of components in the signal.

In the method, a frequency spectrum is calculated for at least a portion of the input signal. This frequency spectrum is used to identify a frequency at which to demodulate the input signal. The demodulated portions of the signal are averaged together to generate an averaged output signal. As can been seen from the experimental results described herein, the method limits the introduction of noise artifacts.

This allows nerve activity to be monitored more accurately, particularly in situations where noise exists, such as when monitoring autonomic nerves.

The improved output signal can be used to determine peaks in nerve activity signals in a more accurate manner. Thus, correlations between nerve activity and physiological activity in a human or an animal subject can be identified more easily. As another example, the improved output signal can be analyzed in order to produce a signal for stimulating a nerve of a human or an animal subject, so that desired physiological responses in a subject can be induced.

Figure 2:
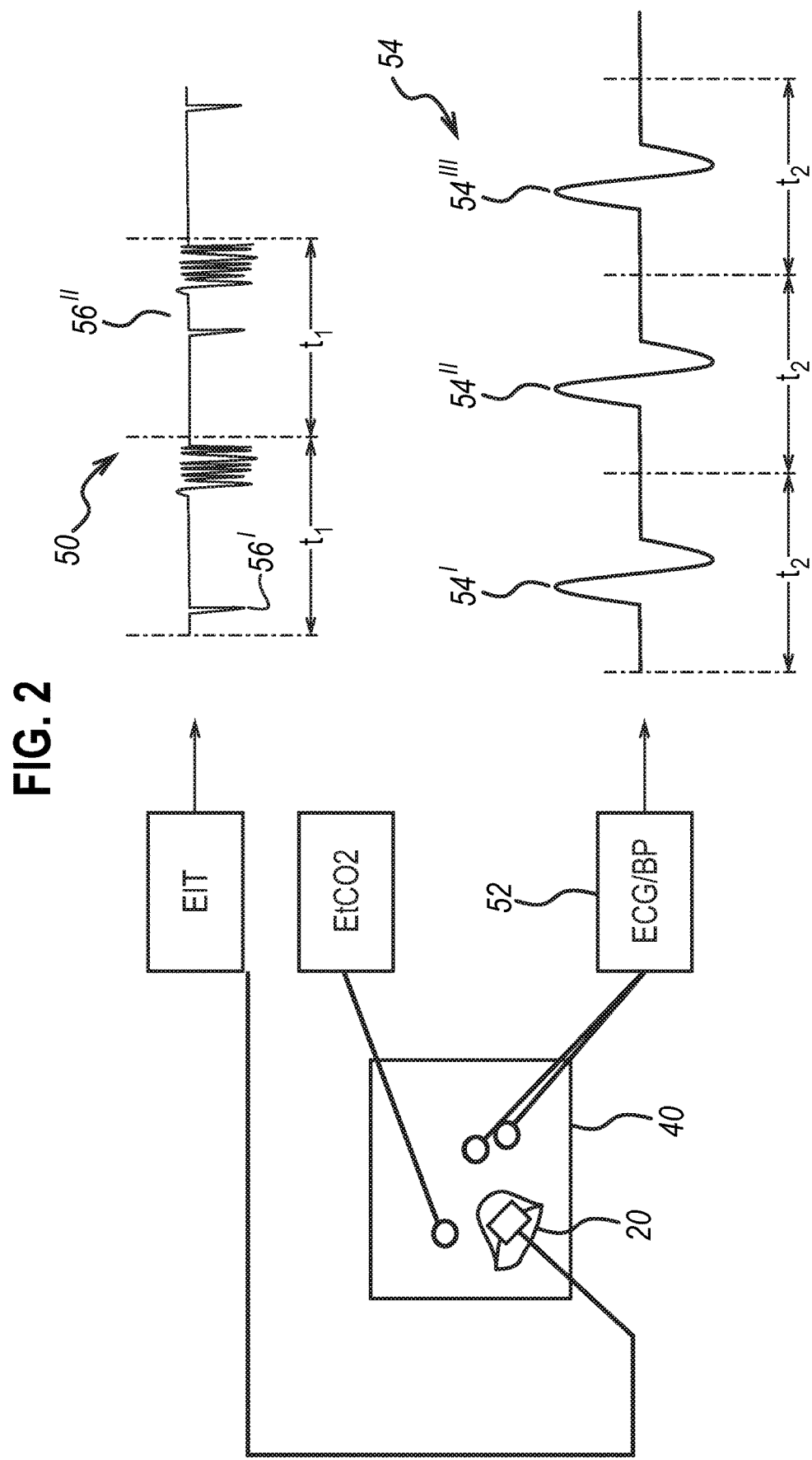
FIG. 2 illustrates a schematic overview of a system for monitoring a peripheral nerve of a human/animal subject and monitoring physiological activity in a human/animal subject.

Referring again to FIG. 2, a physiological sensor 52 can be connected to the sheep 40 in order to measure a physiological activity in the subject. In this example, an electrocardiogram (ECG) monitor and/or a blood pressure (BP) monitor 52 are used to generate a signal 54 indicative of physiological activity in the sheep. In this case, the physiological signal 54 is indicative of tonic activity associated with cardiac and/or pulmonary cycles of the sheep 40.

The EIT signal 50 is produced by applying electric signals (each at a particular frequency) to the electrodes in the cuff 22 and measuring the response signals. The response signals can be demodulated around the frequency at which the electrodes were stimulated In order to generate the EIT signal 50. This, in effect, removes the EIT 'carrier' signal from the response signals. This process is described in greater detail in WO 2016/170327.

The EIT signal 50 comprises a plurality of signal portions 56', 56" each with a period of t1. The physiological signal 54 comprises a plurality of signal portions 54', 54", 54"' each with a period of t2. In this case, the EIT signal 50 and physiological signal 54 illustrate the change in amplitude of nerve and/or physiological activity of the sheep 40 over time.

It is desirable to calculate an average periodic signal from the periodic signal portions 56', 56". This can provide information regarding the general characteristics of each periodic portion of the signal, for instance, by identifying peaks in the periodic signals.

Figure 3:
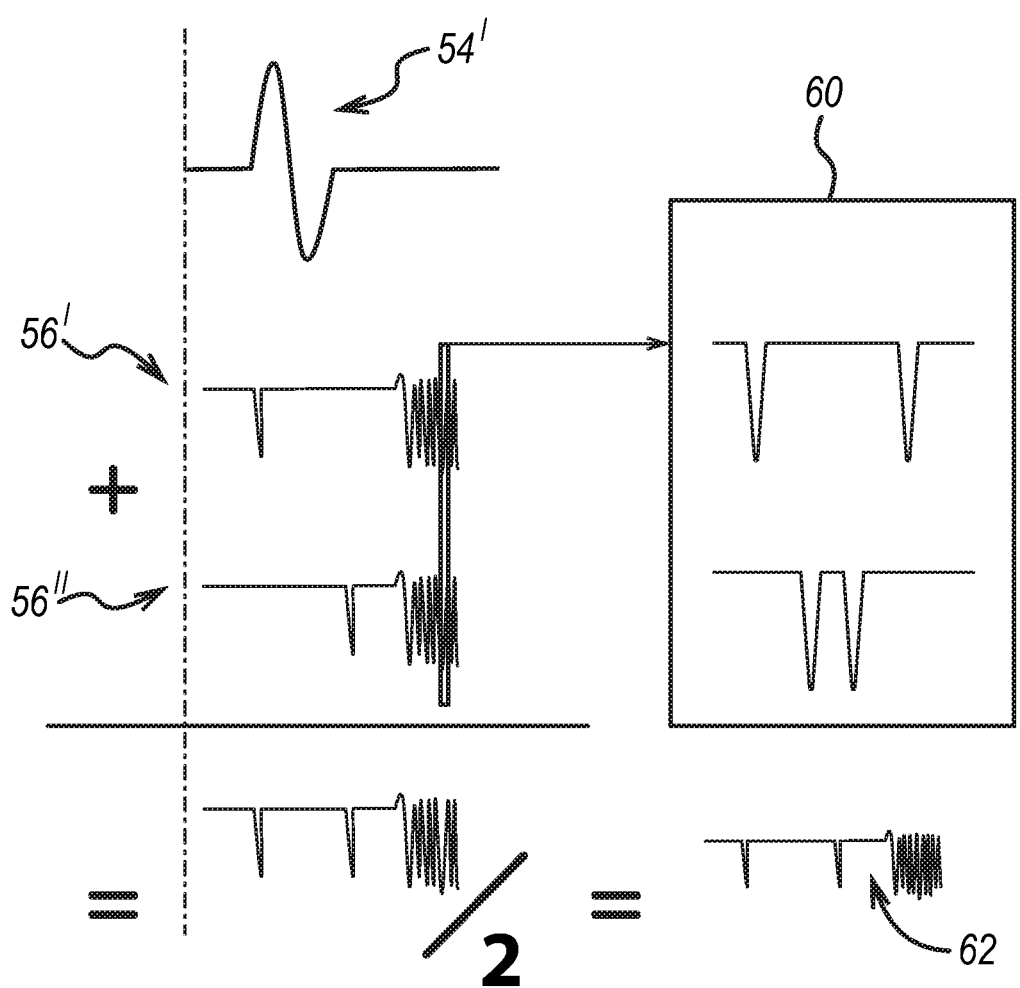
FIG. 3 illustrates a method for averaging signals indicative of activity in a nerve.

A method for calculating an average of the periodic signal portions 56', 56" is illustrated in FIG. 3. This method uses a conventional averaging technique.

The term "periodic" is used herein to refer to certain characteristics of a signal or waveform that substantially repeat over time, as would be understood by a person skilled in the art. However, for the avoidance of doubt "periodic" portions of a signal are considered herein to have a similar duration and/or similar characteristics to one another. Here the term "similar" is used herein to refer to periodic signal portions being at least partially identical to one another over a time period.

Referring to FIG. 3, in the method at least two portions 56', 56" of the EIT signal 50 are identified. As can be seen from the representations of the portions 56', 56" and a magnified view 60 of a slice of the portions 56', 56", the peaks in amplitude within each period of the EIT signal do not necessarily correspond with one another in the time domain. Therefore, if the two portions 56', 56" are summed together and divided by two in order to generate an average of the two portions, this leads to a 'noisy' averaged output signal 62.

As the number of periodic portions of the signal being averaged with one another increases, the amplitude of the averaged signal will eventually reduce to zero due to the random nature of the noise artifacts in the input signal 50. This is particularly relevant for autonomic nerves, where noise artifacts are more prominent, periodicity naturally averages out the signal, and the signal-to-noise ratio (SNR) is lower due to small amplitude action potentials, as discussed previously.

Figure 4:
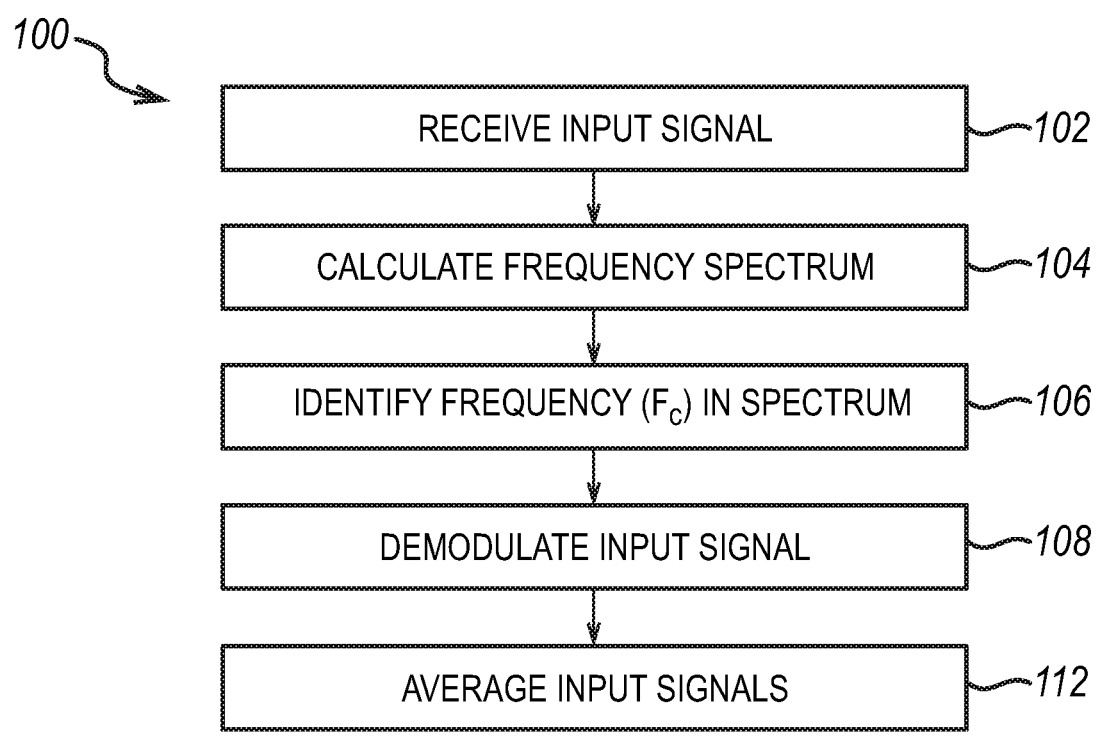
FIG. 4 illustrates a flowchart of a method for reducing the effect of noise artifacts in an averaged output signal indicative of electrical activity in a nerve.
Figure 5:
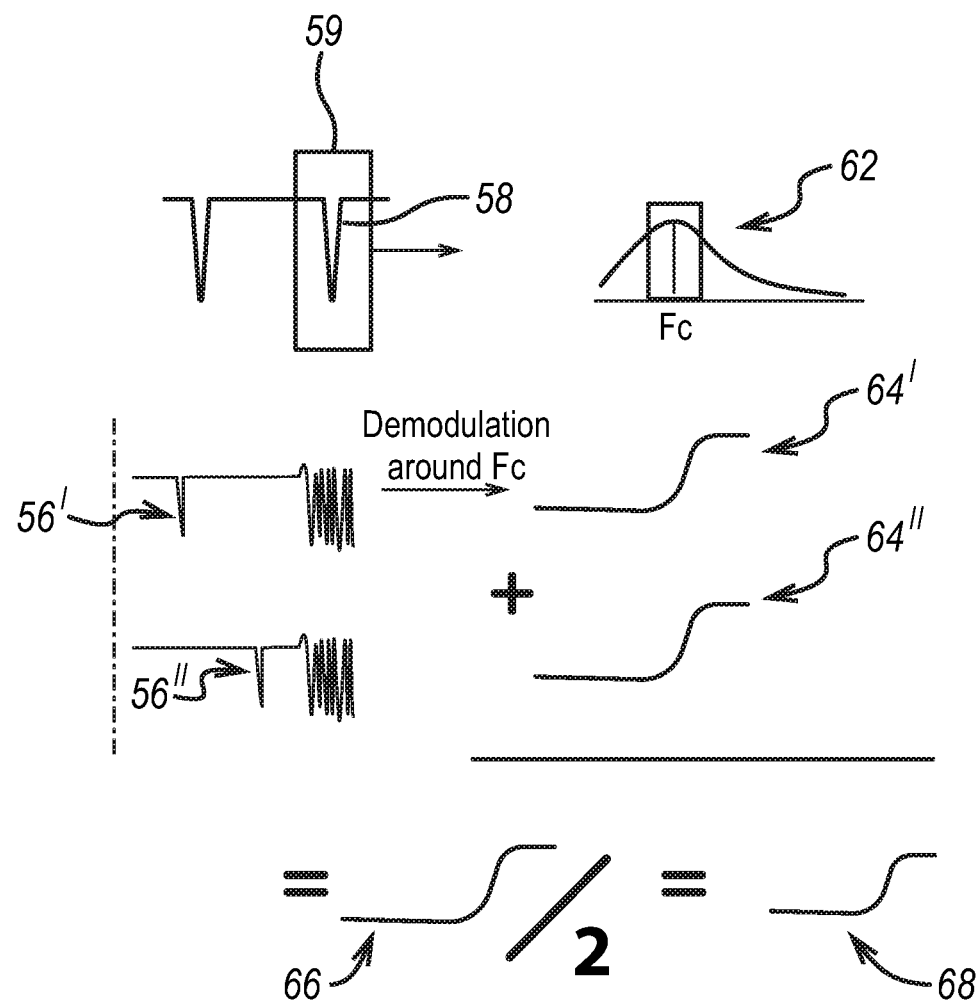
FIG. 5 illustrates a number of inputs and outputs of the method.

Referring to FIGS. 4 and 5, there is provided a method 100 for generating an averaged output signal from an input signal indicative of electrical activity in a nerve. This method has been found to provide improved results in comparison to the method using conventional averaging.

It would be possible to conduct the method described herein in 'real-time', with outputs being generated in response to input data measured from a subject in-situ. However, it would also be possible to conduct the method described herein on the basis of pre-recorded inputs in order to produce the relevant outputs.

Figure 1:
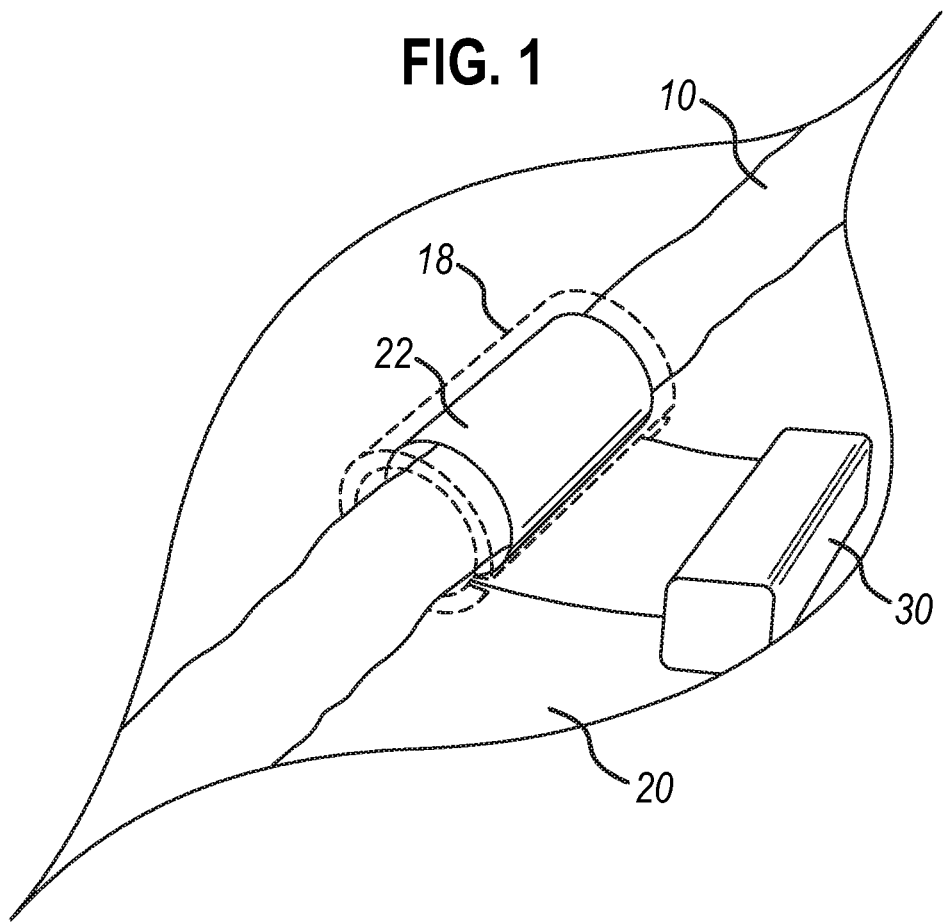
FIG. 1 illustrates a device for monitoring a peripheral nerve of a human or an animal subject.

At 102, an input signal is received. In this case, the input signal is a signal indicative of electrical activity in a nerve. For instance, the input signal may be the EIT signal 50 generated using the device 20 described with reference to FIGS. 1 and 2. In particular, this EIT signal may have been produced using an initial demodulation process for removing the EIT 'carrier' signal.

The EIT signal 50 may comprise periodic portions 56', 56". These periodic portions 56', 56" may be related to periodic portions of a physiological signal 54', such as the signal(s) 54 generated by the ECG and/or the BP devices described in reference to FIG. 2. However, due to the apparent presence of noise in the EIT signal 50, these periodic portions may be difficult to identify.

In this example, a physiological signal is received and the period of periodic portions in this signal is determined. It would, however, be possible to perform the method described herein on the basis of physiological data, such as the heart rate of a subject. In this example, the period of the subject's heart rate could be used instead of the period of the periodic portions determined from an ECG signal of the subject's heart activity.

Therefore, in the method 100 the input signal 50 is partitioned, or in other words 'divided up', into periodic portions 56', 56" based on the period of the periodic parts of the physiological signal 54. In this example, the tonic activity illustrated by the physiological signal 54 has well-defined periodic portions, each with a period of t2. This period t2 is taken to be equal to t1, and the input signal 50 is divided into periodic portions, each with a period t2 which is equal to the period t1 of the periodic portions of the physiological signal. In this way it is possible to establish a relationship between the physiological signal and the input signal. So that periodic portions in the input signal can be identified. In another example, the period of the periodic portions of the input signal could be determined without using the physiological signal. In this case, the input signal would be auto-correlated (i.e. correlated with itself) in order to determine the period.

Although partitioning the input signal 50 could be conducted at this stage, it has been found that better results are produced when the input signal is partitioned at a later stage. This is described in detail below.

At 104, a frequency spectrum of at least a portion of the EIT signal 50 is calculated. The frequency spectrum may be calculated using a Fourier Transform method, or any other suitable method for calculating a frequency spectrum of a signal that would be known to the skilled person.

In one example of this disclosure, the frequency spectrum between 0 Hz to 20 kHz is calculated. In another example, the frequency spectrum between 10 Hz to 3 kHz or 1 Hz to 5 kHz is calculated. This is particularly advantageous, since neutral activity does not usually contain frequencies outside of these ranges. Thus, by limiting the frequency spectrum to these ranges, processing resources can be used more effectively and spurious frequency peaks can be avoided.

In one example, a portion, or in other words a window 59, is positioned across an individual pulse 58 one of the periodic portions 56' 56" of the EIT signal. Then, the frequency spectrum 62 of the individual pulse 58 is calculated by calculating the frequency spectrum inside the window 59.

In another example, a window 59 of a pre-determined length in the time domain is used. This window 59 is placed over successive parts of the input signal 50. A frequency spectrum is calculated for each part of the input signal 50 over which the window 59 is placed. This generates a plurality of frequency spectrums. An example of one such frequency spectrum chart 62 is illustrated in FIG. 5.

Each one of the frequency spectrum charts is associated with the position of the window in the time domain on the input signal 50. This is used to create a three-dimensional matrix. One of the dimensions is indicative of the frequency of the frequency spectrums. Another one of the dimensions is indicative of the amplitude associated with each frequency in the spectrum. The final dimension is indicative of the time associated with each window used to generate each frequency spectrum.

At 106, a frequency Fc is identified in the frequency spectrum(s) 62. In this example, the frequency Fc with the highest amplitude is selected. In another example the frequency associated with a frequency peak is selected. In yet another example, it is possible correlate the frequency spectrum(s) 62 with the physiological signal 54 and, then, select a frequency associated with a frequency peak which is correlated with a characteristic of the physiological signal.

In the example where partitioning of the signal is performed without using he physiological signal, the demodulation frequency Fc can be determined by auto-correlating the input signal. Auto-correlation can also be used to determine suitable partitioning of the signal. In this way, not only the range of frequencies are probed, but also the range of the appropriate expected periods of the physiological cycle are probed. This helps to identify an appropriate period for the input signal within the same routine and using the same criterion.

At 108, the input signal 50 is demodulated around Fc. This generates a demodulated version of the input signal.

At 112, the demodulated version of the input signal is divided into portions, each with the period t2 which was determined from the physiological signal 54. This creates a plurality of demodulated periodic portions 64', 64". Next, the demodulated periodic portions are averaged together. For exemplary purposes two demodulated periodic portions 64', 64" are illustrated. However, the skilled person would appreciate that two or more periodic portions could be used.

In this example, the averaging involves summing the demodulated periodic portions 64', 64" across the time domain. Then, the sum of the portions 66 is divided by the number of demodulated periodic portions that were summed, which in this case is two. It will be appreciated that any other suitable averaging technique could be used that would be known to the skilled person. This generates an averaged output signal 68.

It will be appreciated that the above could be executed in any suitable sequence, in order to generate the averaged output signal. For instance, period portions 56', 56" of the EIT signal may be selected by dividing the input signal into portions of length t2 before demodulating the portions around Fc. This would generate the demodulated periodic portions 64', 64" in a similar manner to that described above. However, it has been found that demodulating the input signal before it is divided into portions for averaging is more efficient and provides more accurate results.

Figure 6:
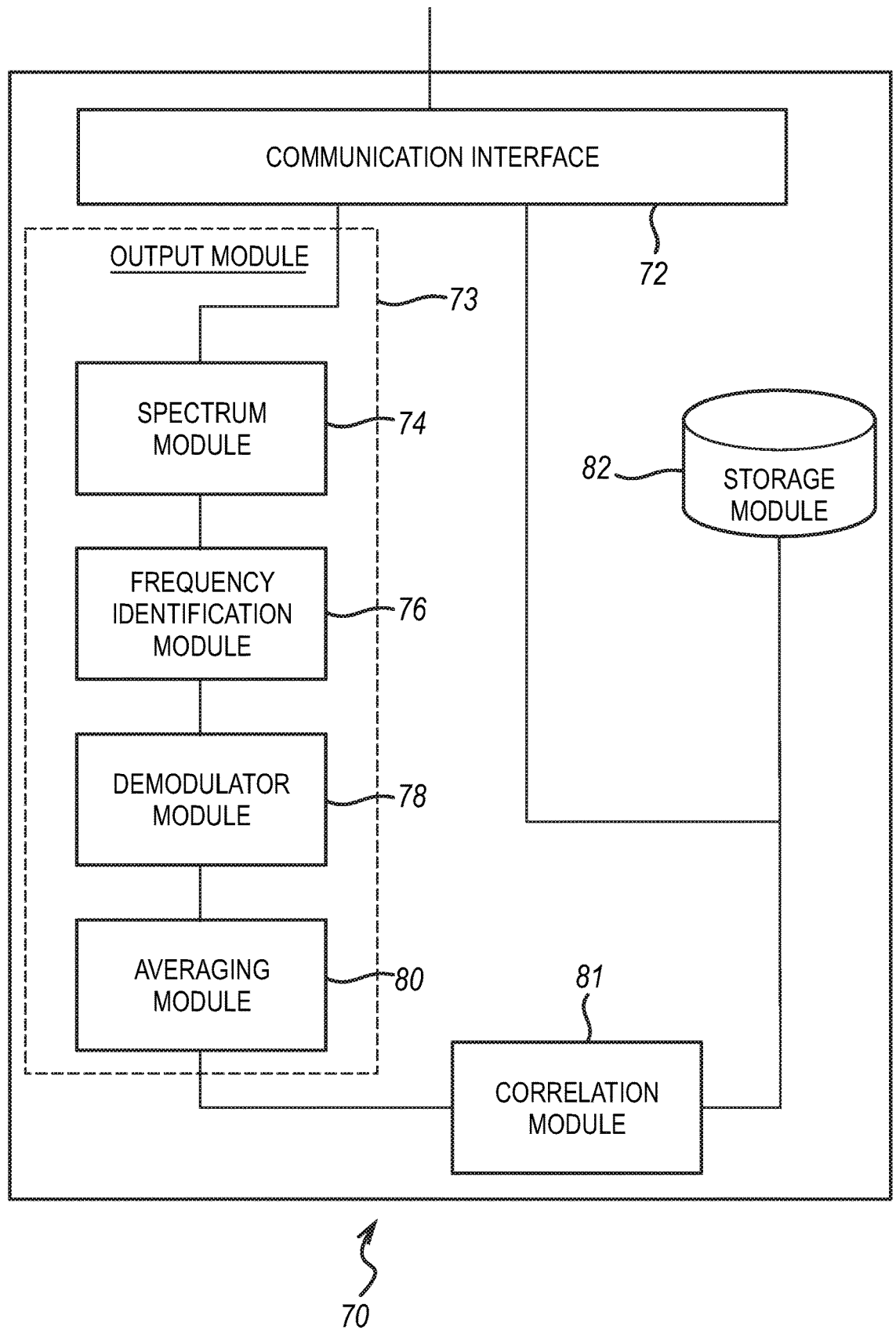
FIG. 6 illustrates a nerve activity monitoring system for executing the method described with reference to FIGS. 4 and 5.

Referring to FIG. 6, there is provided a system 70 for generating an averaged output signal from an input signal indicative of electrical activity in a nerve. The system 70 comprises a communication interface 72, an output module 73, a correlation module 81 and a storage module 82.

The communication interface 72 is configured to receive the input signal indicative of electrical (or physiological) activity in a nerve, as described with reference to 02 In FIG. 4. In this example, the communication interface 72 is configured to receive the EIT signal from the device 20 described with reference to FIGS. 1 and 2. However, it will be appreciated that the input signal could be received from any other suitable device or the system 70 and communication interface 72 could be integrated into the device which acquires the signal from the nerve. The communication interface 72 may receive the input signal via any suitable wired and/or wireless communication protocol. The communication interface 72 is also configured to receive the physiological signal 54.

The output module 73 is arranged to perform the process described with reference to FIG. 4, and comprises a spectrum module 74, a frequency identification module 76, a demodulator module 78, and an averaging module 80. The spectrum module 74 is arranged to perform the frequency spectrum calculation described with reference to 104 in FIG. 4, in respect of at least a portion of the received input signal. The frequency spectrum calculation generates a frequency spectrum for the frequency identification module 76, which identifies a frequency (Fc) within the spectrum, as described with reference to 106 in FIG. 4.

The demodulation module 76 is arranged to perform the demodulation process described with reference to 108 in FIG. 4. This generates a plurality of demodulated periodic portions 64', 64" of the input signal that are provided to the averaging module 80.

The averaging module 80 is arranged to perform the averaging process described with reference to 112 in FIG. 4. This generates an averaged output signal which is output by the averaging module. This averaged output signal may be output to the storage module 82 for later analysis. In addition or alternatively to storing the averaged output signal, this signal may be provided to the communications interface so that the output signal can be transmitted to an external device. For instance, the system 70 may output the averaged signal to a display device for visual presentation to a user, or the system may output the averaged signal to another computing device for further analysis. The correlation module 81 is arranged to correlate the identified periodic portions of the input signal with the physiological signal. The correlation module 81 can be arranged to generate electrical signals for an electrode based on the correlation of the identified periodic portions of the input signal with the physiological signal. These electrical signals can be output by the communication interface 72.

Figure 7A:
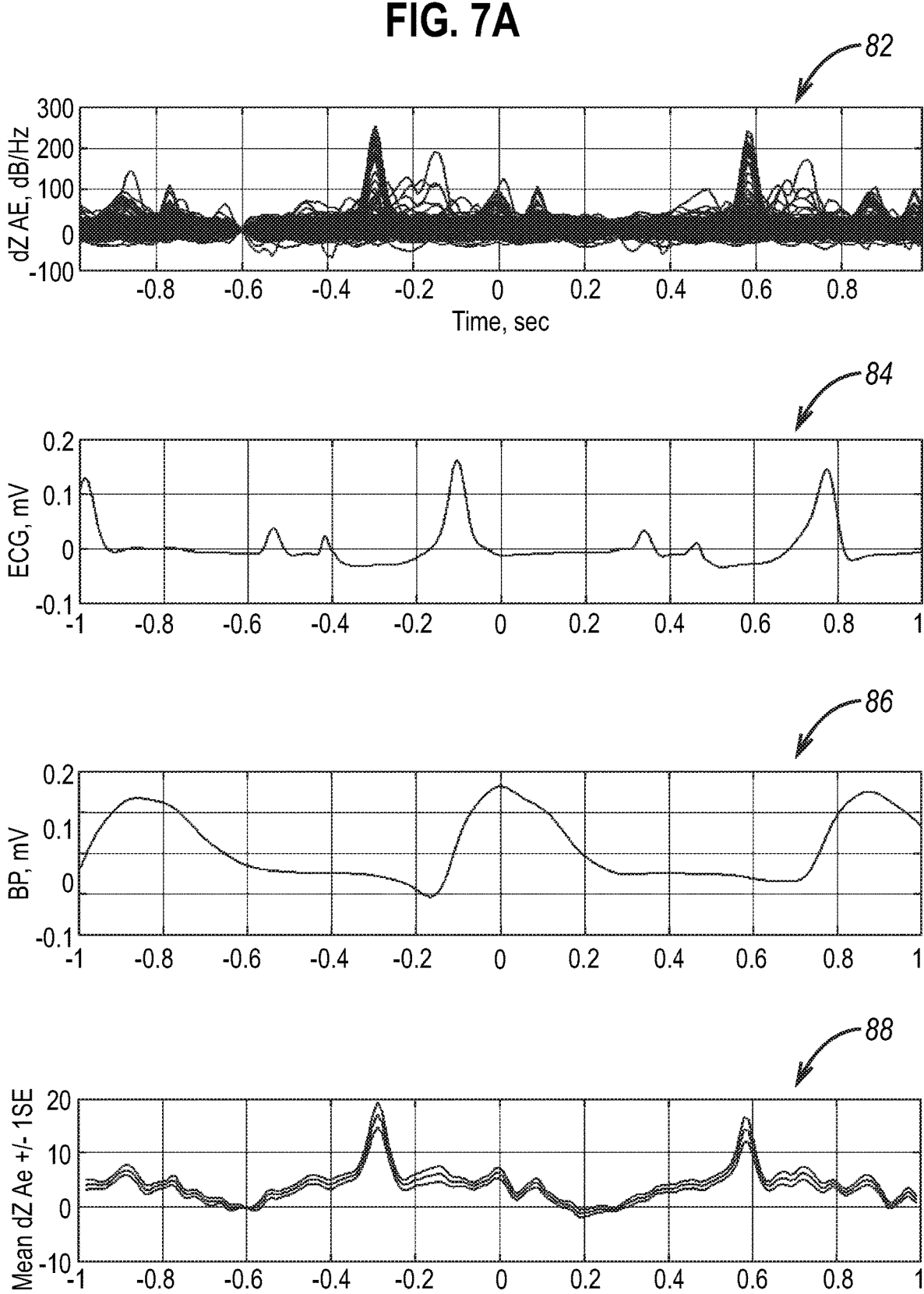
FIG. 7A illustrates various recordings of nerve activity and physiological activity in a sheep.
Figure 7B:
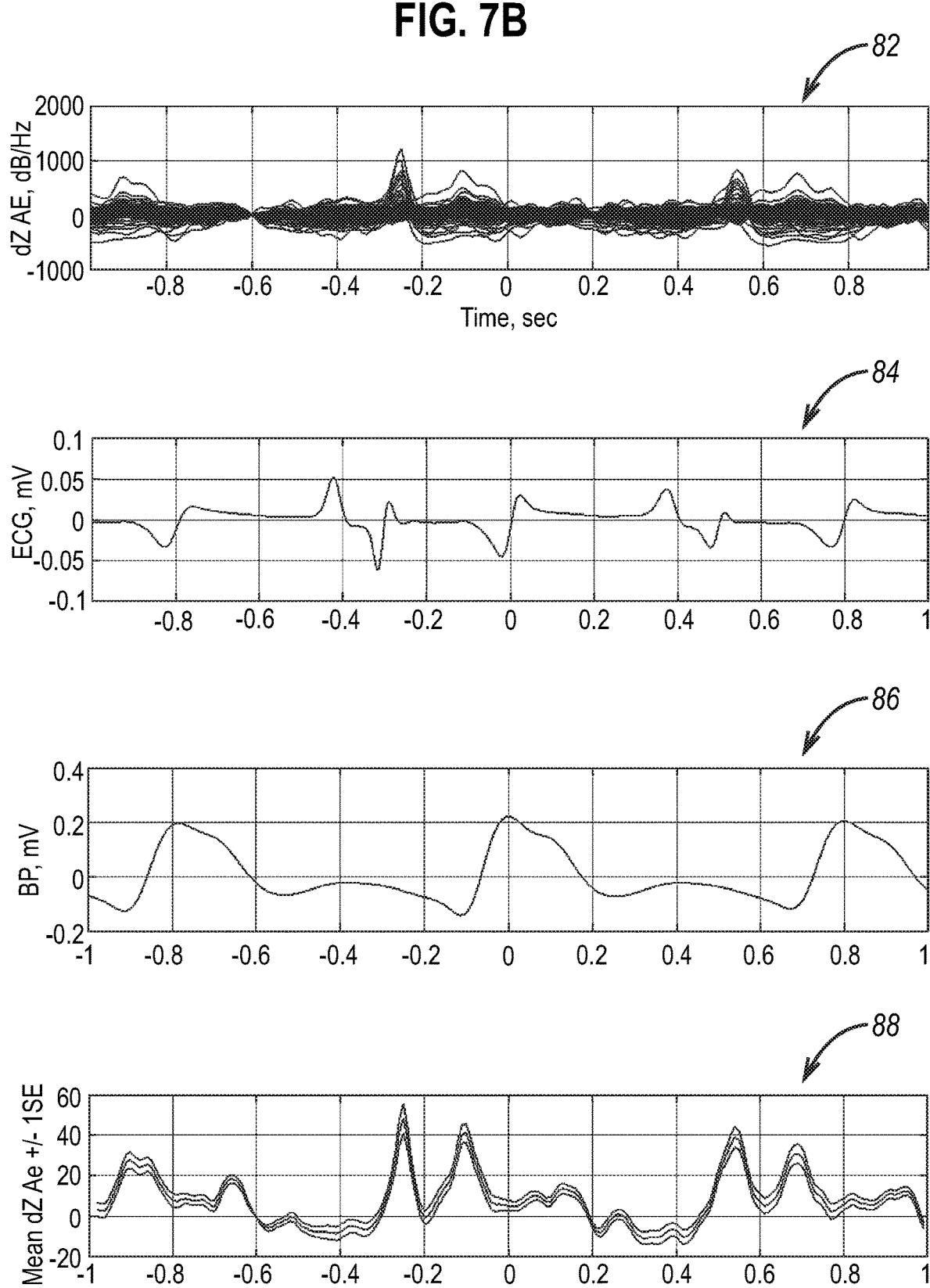
FIG. 7B illustrates various recordings of nerve activity and physiological activity in another sheep.
Figure 7C:
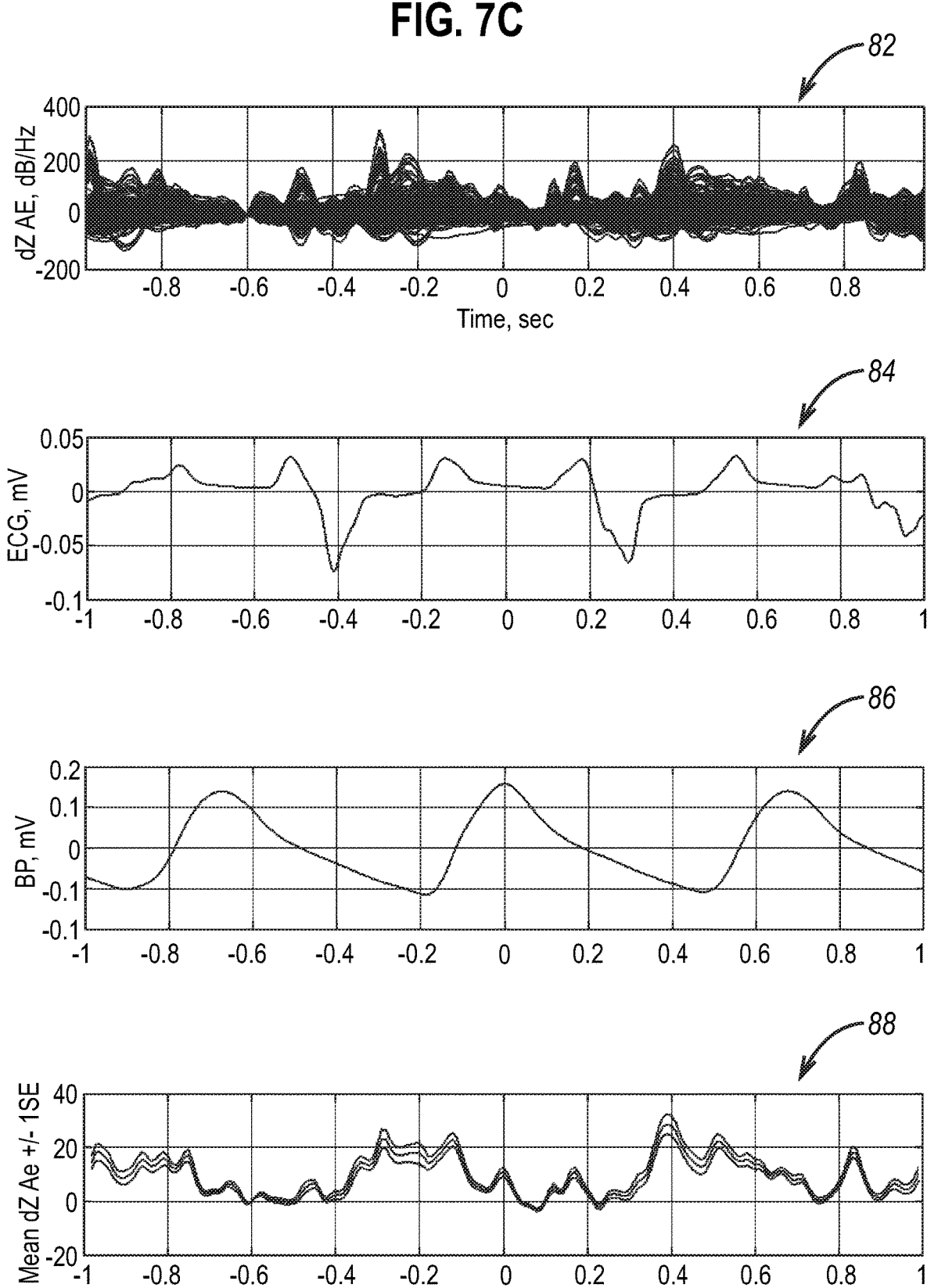
FIG. 7C illustrates various recordings of nerve activity and physiological activity in yet another sheep.

FIGS. 7A, 7B and 7C, illustrate a set of charts that demonstrate one potential application for the averaging method described herein. However, it will be appreciated that the method and apparatus set out above has a myriad of potential applications, with one important aspect being the reduction of noise in periodic signals.

Referring to FIGS. 7A-7C, there are nerve signal charts 82 each illustrating a number of periodic portions of an input signal derived from a sheep's nerve activity. These nerve charts 82 show the input signal collected from a plurality of different electrodes in a cuff, such as the cuff 22 illustrated in FIG. 1. Each one of the input signals shown in the nerve charts 82 have been generated using the averaging method described above with reference to FIGS. 4 and 5.

FIGS. 7A-7C also show averaged nerve signal charts 88. Each one of these charts 88 illustrate an average of the signals from each of the electrodes illustrated in the corresponding nerve signal chart 82. There are ECG charts 84, each illustrating the electrical activity of the sheep's heart, and blood pressure charts 86 illustrating the sheep's blood pressure over the period of the input signals. The time axis in each one of these charts is centered on a peak identified in the sheep's blood pressure reading. Each set of charts shown in FIGS. 7A, 7B and 7C illustrate charts relating to a different sheep.

In this example, it can be seen that the maximum activity of the nerve is present at −0.32 s (+/−0.3 s) before the BP peak. Therefore, it is possible to determine that there is a correlation between the nerve activity and the blood pressure in the sheep. In particular, it is possible to determine that a specific activity in the nerve leads to a specific physiological response. Thus, it may be possible to reproduce the measured nerve activity in order to reproduce the physiological response correlated with that nerve activity.

Although methods and systems have been described above in relation to the vagus nerve of a subject, it will be appreciated that the methods and system are suitable for other nerves. For example, the methods and systems described herein may be applied to the autonomic nervous system, including sympathetic and parasympathetic, and post ganglionic, and pre-ganglionic components, and ganglionic components, and afferent and efferent branches.

In addition, the methods and systems described herein may be applied to the somatic nervous system, including afferent and efferent branches, ganglia, and spinal roots. Furthermore, the methods and systems described herein may be applied to nerve targets including but not limited to: vagus and branches, sympathetic chain (cervical, thoracic, and lumbar, and ganglia), pelvic (including major pelvic ganglion), pudendal, hypogastric, greater 10 splanchnic and branches, carotid sinus nerve, hypoglossal, glossopharyngeal, sciatic (and branches), ulnar and median, phrenic, spinal nerves, cranial nerves.

In additional examples, the physiological activities, signals and/or responses can include (but are not limited to): heart rate and ECG output, ventilation, plural pressure, systolic and diastolic blood pressure, electromyography (EMG) skeletal and smooth muscle from specific motor units, bladder pressure, rectal pressure, smooth muscle motion (e.g. peristalsis), measurements taken from the blood (e.g. hormones, cytokines, chemokines, cell type expressions, etc.).

Furthermore, the methods and systems described herein can be implemented in an implantable device and may be a part of the system that provides images of the periodic neural activity. These images can be provided in 'real-time' or 'semi-real-time'.

The methods and systems can be used for diagnostic surgical implementation for first time optimized electrode placement, temporal therapy adjustment over health/disease progression or electrode movement, patient specific therapy (dose dependency), automated and/or clinician and/or patient directed closed-loop delivery of the neuromodulation therapy.

The methods and systems can provide images of the periodic activity during implantation to assist therapeutic parameters selection and/or may sense the raw nerve activity signals in real-time, in order to provide a therapeutic decision based on the neural events. This may occur in 'real-time' and/or in a 'closed-loop' system.

An Implantable Device/System for Implementing Embodiments of the Disclosure

Figure 8:
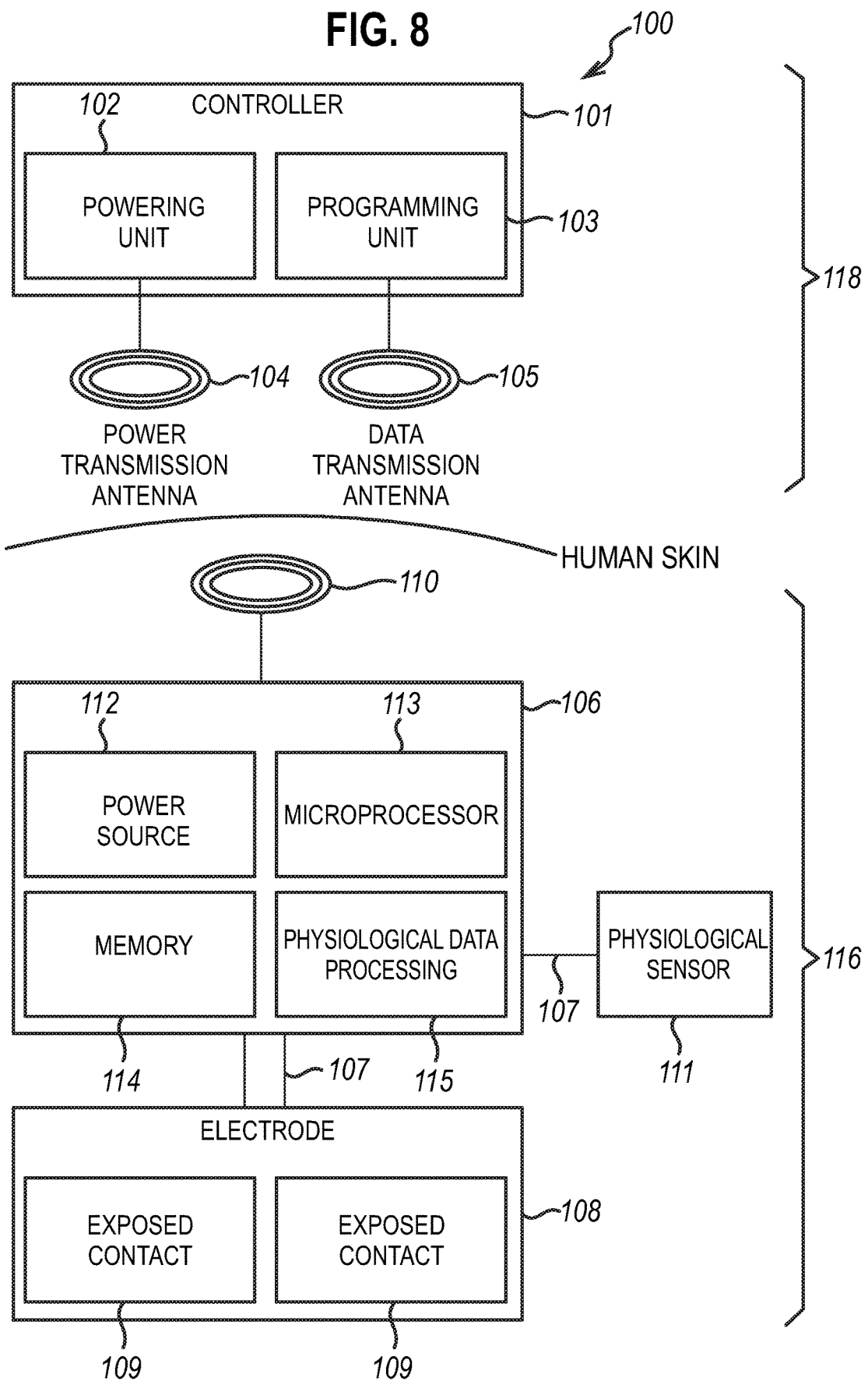
FIG. 8 illustrates an overview of the system.

An implantable system according to the disclosure comprises an implantable device (e.g. implantable device 106 of FIG. 8). The implantable device comprises at least one neural interfacing element such as a transducer, for example an electrode (e.g. electrode 108), suitable for placement on, in, or around a nerve. The implantable system also can comprise a processor (e.g. microprocessor 113) coupled to the at least one neural interfacing element.

The at least one neural interfacing element may take many forms, and includes any component which, when used in an implantable device or system for implementing embodiments of the disclosure, is capable of applying a stimulus or other signal that modulates electrical activity in a nerve.

The various components of the implantable system can be part of a single physical device, either sharing a common housing or being a physically separated collection of interconnected components connected by electrical leads (e.g. leads 107). As an alternative, however, embodiments of the disclosure may use a system in which the components are physically separate, and communicate wirelessly. Thus, for instance, the at least one neural interfacing element (e.g. electrode 108) and the implantable device (e.g. implantable device 106) can be part of a unitary device, or together may form an implantable system (e.g. implantable system 116). In both cases, further components may also be present to form a larger device or system (e.g. system 100).

Suitable Forms of a Modulating Signal

Embodiments of the disclosure use a signal applied via one or more neural interfacing elements (e.g. electrode 108) placed in signaling contact with a nerve.

Signals applied according to the disclosure are ideally non-destructive. As used herein, a "non-destructive signal" is a signal that, when applied, does not irreversibly damage the underlying neural signal conduction ability of the nerve. That is, application of a non-destructive signal maintains the ability of the nerve (e.g. a nerve) or fibers thereof, or other nerve tissue to which the signal is applied, to conduct action potentials when application of the signal ceases, even if that conduction is in practice artificially stimulated as a result of application of the non-destructive signal.

The signal will usually be an electrical signal, which may be, for example, a voltage or current waveform. The at least one neural interfacing element (e.g. electrode 108) of the implantable system (e.g. implantable system 116) is configured to apply the electrical signals to a nerve, or a part thereof. However, electrical signals are just one way of implementing embodiments of the disclosure, as is further discussed below.

An electrical signal can take various forms, for example, a voltage or current. In certain such embodiments the signal applied comprises a direct current (DC), such as a charge balanced direct current, or an alternating current (AC) waveform, or both a DC and an AC waveform. A combination of charge balanced DC and AC is particularly useful, with the DC being applied for a short initial period after which only AC is used. As used herein, "charge-balanced" in relation to a DC current is taken to mean that the positive or negative charge introduced into any system (e.g. a nerve) as a result of a DC current being applied is balanced by the introduction of the opposite charge in order to achieve overall (net) neutrality. In other words, a charge-balance DC current includes a cathodic pulse and an anodic pulse.

In certain embodiments, the DC waveform or AC waveform may be a square, sinusoidal, triangular, trapezoidal, quasitrapezodial or complex waveform. The DC waveform may alternatively be a constant amplitude waveform. In certain embodiments the electrical signal is an AC sinusoidal waveform. In other embodiments, waveform comprise one or more pulse trains, each comprising a plurality of charge-balanced biphasic pulses.

The signal may be applied in bursts. The range of burst durations may be from seconds to hours; applied continuously in a duty cycled manner from 0.01% to 100%, with a predetermined time interval between bursts. The electric signal may be applied as a step change or as a ramp change in current or intensity. Particular signal parameters for modulating (e.g. stimulating) a nerve are further described below.

Modulation of the neural activity of the nerve can be achieved using electrical signals which serve to replicate the normal neural activity of the nerve.

Signal parameters for modulating neural activity

In all of the above examples, a signal generator may be configured to deliver an electrical signal for modulating (e.g. stimulating) a nerve (e.g. the ICN). In the present application, the signal generator is configured to apply an electrical signal with certain signal parameters to modulate (e.g. stimulate) neural activity in a nerve (e.g. the ICN). Signal parameters for modulating (e.g. stimulating) the nerve, which are described herein, may include waveform, amplitude and frequency.

It will be appreciated by the skilled person that the current amplitude of an applied electrical signal necessary to achieve the intended modulation of the neural activity will depend upon the positioning of the electrode and the associated electrophysiological characteristics (e.g. impedance). It is within the ability of the skilled person to determine the appropriate current amplitude for achieving the intended modulation of the neural activity in a given subject.

Electrodes

As mentioned above, the implantable system comprises at least one neural interfacing element, and the neural interfacing element can be an electrode 108. The neural interface is configured to at least partially and in some embodiments fully circumvent the nerve. The geometry of the neural interface is defined in part by the anatomy of the nerve or by the structure that the neural interface is interfacing or associated with.

In some embodiments (for example, FIG. 8), electrode 108 may be coupled to implantable device 106 of implantable system 116 via electrical leads 107. Alternatively, implantable device 106 may be directly integrated with the electrode 108 without leads. In any case, implantable device 106 may comprise DC current blocking output circuits, optionally based on capacitors and/or inductors, on all output channels (e.g. outputs to the electrode 108, or physiological sensor 111). Electrode 108 may be shaped as one of: a rectangle, an oval, an ellipsoid, a rod, a straight wire, a curved wire, a helically wound wire, a barb, a hook, or a cuff. In addition to electrode 108 which, in use, is located on, in, or near a nerve (e.g. the ICN), there may also be a larger indifferent electrode placed 119 (not shown) in the adjacent tissue.

In some embodiments, electrode 108 may contain at least two electrically conductive exposed contacts 109 configured, in use, to be placed on, in, or near a nerve. Exposed contacts 109 may be positioned, in use, transversely along the axis of a nerve.

Microprocessor

The implantable system 116, in particular the implantable device 106, may comprise a processor, for example microprocessor 113. Microprocessor 113 may be responsible for triggering the beginning and/or end of the signals delivered to the nerve (e.g., a nerve) by the at least one neural interfacing element. Optionally, microprocessor 113 may also be responsible for generating and/or controlling the parameters of the signal.

Microprocessor 113 may be configured to operate in an open-loop fashion, wherein a pre-defined signal (e.g. as described above) is delivered to the nerve at a given periodicity (or continuously) and for a given duration (or indefinitely) with or without an external trigger, and without any control or feedback mechanism. Alternatively, microprocessor 113 may be configured to operate in a closed-loop fashion, wherein a signal is applied based on a control or feedback mechanism. As described elsewhere herein, the external trigger may be an external controller 101 operable by the operator to initiate delivery of a signal.

Microprocessor 113 of the implantable system 116, in particular of the implantable device 106, may be constructed so as to generate, in use, a preconfigured and/or operator-selectable signal that is independent of any input. In some embodiments, however, microprocessor 113 is responsive to an external signal, for example information (e.g. data) pertaining to one or more physiological parameters of the subject.

Microprocessor 113 may be triggered upon receipt of a signal generated by an operator, such as a physician or the subject in which the device 116 is implanted. To that end, the implantable system 116 may be part of a system which additionally comprises an external system 118 comprising a controller 101. An example of such a system is described below with reference to FIG. 8.

External system 118 of system 100 is external the implantable system 116 and external to the subject, and comprises controller 101. Controller 101 may be used for controlling and/or externally powering implantable system 116. To this end, controller 101 may comprise a powering unit 102 and/or a programming unit 103. The external system 118 may further comprise a power transmission antenna 104 and a data transmission antenna 105, as further described below.

The controller 101 and/or microprocessor 113 may be configured to apply any one or more of the above signals to the nerve intermittently or continuously. Intermittent application of a signal involves applying the signal in an (on-off)n pattern, where n>1. For instance, the signal can be applied continuously for at least 5 days, optionally at least 7 days, before ceasing for a period (e.g. 1 day, 2 days, 3 days, 1 week, 2 weeks, 1 month), before being again applied continuously for at least 5 days, etc. Thus the signal is applied for a first time period, then stopped for a second time period, then reapplied for a third time period, then stopped for a fourth time period, etc. In such an embodiment, the first, second, third and fourth periods run sequentially and consecutively. The duration of the first, second, third and fourth time periods is independently selected. That is, the duration of each time period may be the same or different to any of the other time periods. In certain such embodiments, the duration of each of the first, second, third and fourth time periods may be any time from 1 second (s) to 10 days (d), 2 s to 7 d, 3 s to 4 d, 5 s to 24 hours (24 h), 30 s to 12 h, 1 min to 12 h, 5 min to 8 h, 5 min to 6 h, 10 min to 6 h, 10 min to 4 h, 30 min to 4 h, 1 h to 4 h. In certain embodiments, the duration of each of the first, second, third and fourth time periods is 5 s, 10 s, 30 s, 60 s, 2 min, 5 min, 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 2 d, 3 d, 4 d, 5 d, 6 d, 7 d.

In certain embodiments, the signal is applied by controller 101 and/or microprocessor for a specific amount of time per day. In certain such embodiments, the signal is applied for 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h per day. In certain such embodiments, the signal is applied continuously for the specified amount of time.

In certain alternative such embodiments, the signal may be applied discontinuously across the day, provided the total time of application amounts to the specified time.

Continuous application may continue indefinitely, e.g. permanently. Alternatively, the continuous application may be for a minimum period, for example the signal may be continuously applied for at least 5 days, or at least 7 days.

Whether the signal applied to the nerve is controlled by controller 101, or whether the signal is continuously applied directly by microprocessor 113, although the signal might be a series of pulses, the gaps between those pulses do not mean the signal is not continuously applied.

In certain embodiments, the signal is applied when the subject is in a specific state e.g. when the subject is awake, when the subject is asleep, prior to and/or after the ingestion of food, prior to and/or after the subject undertakes exercise, etc.

The various embodiments for timing for modulation of neural activity in the nerve can all be achieved using controller 101 in a device/system of the disclosure.

Other Components of the System Including the Implantable Device

In addition to the aforementioned electrode 108 and microprocessor 113, the implantable system 116 may comprise one or more of the following components: implantable transceiver 110; physiological sensor 111; power source 112; memory 114; and physiological data processing module 115. Additionally or alternatively, the physiological sensor 111; memory 114; and physiological data processing module 115 may be part of a sub-system external to the implantable system. Optionally, the external sub-system may be capable of communicating with the implantable system, for example wirelessly via the implantable transceiver 110.

In some embodiments, one or more of the following components may be contained in the implantable device 106: power source 112; memory 114; and a physiological data processing module 115.

The power source 112 may comprise a current source and/or a voltage source for providing the power for the signal delivered to a nerve by the electrode 108. The power source 112 may also provide power for the other components of the implantable device 106 and/or implantable system 116, such as the microprocessor 113, memory 114, and implantable transceiver 110. The power source 112 may comprise a battery, the battery may be rechargeable.

It will be appreciated that the availability of power is limited in implantable devices, and embodiments of the disclosure have been devised with this constraint in mind. The implantable device 106 and/or implantable system 116 may be powered by inductive powering or a rechargeable power source.

System Including Implantable Device

With reference to FIG. 8, the implantable device 106 of the disclosure may be part of a system 110 that includes a number of subsystems, for example the implantable system 116 and the external system 118. The external system 118 may be used for powering and programming the implantable system 116 and/or the implantable device 106 through human skin and underlying tissues.

The external subsystem 118 may comprise, in addition to controller 101, one or more of: a powering unit 102, for wirelessly recharging the battery of power source 112 used to power the implantable device 106; and, a programming unit 103 configured to communicate with the implantable transceiver 110. The programming unit 103 and the implantable transceiver 110 may form a communication subsystem. In some embodiments, powering unit 102 is housed together with programming unit 103. In other embodiments, they can be housed in separate devices.

The external subsystem 118 may also comprise one or more of: power transmission antenna 104; and data transmission antenna 105. Power transmission antenna 104 may be configured for transmitting an electromagnetic field at a low frequency (e.g., from 30 kHz to 10 MHz). Data transmission antenna 105 may be configured to transmit data for programming or reprogramming the implantable device 106, and may be used in addition to the power transmission antenna 104 for transmitting an electromagnetic field at a high frequency (e.g., from 1 MHz to 10 GHz). The temperature in the skin will not increase by more than 2 degrees Celsius above the surrounding tissue during the operation of the power transmission antenna 104. The at least one antennae of the implantable transceiver 110 may be configured to receive power from the external electromagnetic field generated by power transmission antenna 104, which may be used to charge the rechargeable battery of power source 112.

The power transmission antenna 104, data transmission antenna 105, and the at least one antennae of implantable transceiver 110 have certain characteristics such a resonant frequency and a quality factor (Q). One implementation of the antenna(e) is a coil of wire with or without a ferrite core forming an inductor with a defined inductance. This inductor may be coupled with a resonating capacitor and a resistive loss to form the resonant circuit. The frequency is set to match that of the electromagnetic field generated by the power transmission antenna 105. A second antenna of the at least one antennae of implantable transceiver 110 can be used in implantable system 116 for data reception and transmission from/to the external system 118. If more than one antenna is used in the implantable system 116, these antennae are rotated 30 degrees from one another to achieve a better degree of power transfer efficiency during slight misalignment with the with power transmission antenna 104.

External system 118 may comprise one or more external body-worn physiological sensors 121 (not shown) to detect signals indicative of one or more physiological parameters. The signals may be transmitted to the implantable system 116 via the at least one antennae of implantable transceiver 110. Alternatively or additionally, the signals may be transmitted to the external system 116 and then to the implantable system 116 via the at least one antennae of implantable transceiver 110. As with signals indicative of one or more physiological parameters detected by the implanted physiological sensor 111, the signals indicative of one or more physiological parameters detected by the external sensor 121 may be processed by the physiological data processing module 115 to determine the one or more physiological parameters and/or stored in memory 114 to operate the implantable system 116 in a closed-loop fashion. The physiological parameters of the subject determined via signals received from the external sensor 121 may be used in addition to alternatively to the physiological parameters determined via signals received from the implanted physiological sensor 111.

For example, in a particular embodiment a detector external to the implantable device may include an optical detector including a camera capable of imaging the eye and determining changes in physiological parameters, in particular the physiological parameters described above. As explained above, in response to the determination of one or more of these physiological parameters, the detector may trigger delivery of signal to a nerve by the electrode 108, or may modify the parameters of the signal being delivered or a signal to be delivered to a nerve by the electrode 108 in the future.

The system 100 may include a safety protection feature that discontinues the electrical stimulation of a nerve in the following exemplary events: abnormal operation of the implantable system 116 (e.g. overvoltage); abnormal readout from an implanted physiological sensor 111 (e.g. temperature increase of more than 2 degrees Celsius or excessively high or low electrical impedance at the electrode-tissue interface); abnormal readout from an external body-worn physiological sensor 121 (not shown); or abnormal response to stimulation detected by an operator (e.g. a physician or the subject). The safety precaution feature may be implemented via controller 101 and communicated to the implantable system 116, or internally within the implantable system 116.

The external system 118 may comprise an actuator 120 (not shown) which, upon being pressed by an operator (e.g. a physician or the subject), will deliver a signal, via controller 101 and the respective communication subsystem, to trigger the microprocessor 113 of the implantable system 116 to deliver a signal to the nerve by the electrode 108.

System 100 of the disclosure, including the external system 118, but in particular implantable system 116, can be made from, or coated with, a biostable and biocompatible material. This means that the device/system is both protected from damage due to exposure to the body's tissues and also minimizes the risk that the device/system elicits an unfavorable reaction by the host (which could ultimately lead to rejection). The material used to make or coat the device/system should ideally resist the formation of biofilms. Suitable materials include, but are not limited to, poly(p-xylylene) polymers (known as Parylenes) and polytetrafluoroethylene.

The implantable device 116 of the disclosure will generally weigh less than 50 g.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from a definition of the disclosure.

The term "about" in relation to a numerical value x is optional and means, for example, x+10%.

Unless otherwise indicated each embodiment as described herein may be combined with another embodiment as described herein.

The methods described herein may be performed by software in machine readable form on a tangible storage medium e.g. in the form of a computer program comprising computer program code means adapted to perform all of any of the methods described herein when the program is run on a computer and where the computer program may be embodied on a computer readable medium. Examples of tangible (or non-transitory) storage media include disks, thumb drives, memory cards etc and do not include propagated signals. The software can be suitable for execution on a parallel processor or a serial processor such that the method may be carried out in any suitable order, or simultaneously. This acknowledges that firmware and software can be valuable, separately tradable commodities. It is intended to encompass software, which runs on or controls "dumb" or standard hardware, to carry out the desired functions. It is also intended to encompass software which "describes" or defines the configuration of hardware, such as HDL (hardware description language) software, as is used for designing silicon chips, or for configuring universal programmable chips, to carry out desired functions.

It will be appreciated that the modules described herein may be implemented in hardware or in software. Furthermore, the modules may be implemented at various locations throughout the system.

Those skilled in the art will realize that storage devices utilized to store program instructions can be distributed across a network. For example, a remote computer may store an example of the process described as software. A local or terminal computer may access the remote computer and download a part or all of the software to run the program. Alternatively, the local computer may download pieces of the software as needed, or execute some software instructions at the local terminal and some at the remote computer (or computer network). Those skilled in the art will also realize that by utilizing conventional techniques known to those skilled in the art that all, or a portion of the software instructions may be carried out by a dedicated circuit, such as a DSP, programmable logic array, or the like.

Any range or device value given herein may be extended or altered without losing the effect sought, as will be apparent to the skilled person.

It will be understood that the benefits and advantages described above may relate to one embodiment or may relate to several embodiments. The embodiments are not limited to those that solve any or all of the stated problems or those that have any or all of the stated benefits and advantages.

Any reference to 'an' item refers to one or more of those items. The term 'comprising' is used herein to mean including the method blocks or elements identified, but that such blocks or elements do not comprise an exclusive list and a method or apparatus may contain additional blocks or elements.

The steps of the methods described herein may be carried out in any suitable order, or simultaneously where appropriate. Additionally, individual blocks may be deleted from any of the methods without departing from the spirit and scope of the subject matter described herein. Aspects of any of the examples described above may be combined with aspects of any of the other examples described to form further examples without losing the effect sought. Any of the module described above may be implemented in hardware or software.

It will be understood that the above description of embodiments is given by way of example only and that various modifications may be made by those skilled in the art. Although various embodiments have been described above with a certain degree of particularity, or with reference to one or more individual embodiments, those skilled in the art could make numerous alterations to the disclosed embodiments without departing from the scope of this invention.

The invention claimed is:

1. A nerve activity monitoring method comprising:
receiving an input signal indicative of detection of electrical activity in a nerve of a subject;
receiving physiological data indicative of physiological activity in the subject;
establishing a relationship between the physiological data and the input signal;
identifying a plurality of periodic portions in the input signal based on the relationship between the physiological data and the input signal; and
outputting the periodic portions identified by averaging the plurality of periodic portions of the input signal together to generate an averaged signal, wherein averaging the plurality of periodic portions comprises:
calculating a frequency spectrum of at least a portion of the input signal;
identifying a demodulation frequency within the frequency spectrum;
demodulating at least two periodic portions of the input signal based on the demodulation frequency, to generate at least two demodulated signal portions; and
averaging the at least two demodulated signal portions, to generate the averaged signal.

2. The method according to claim 1, wherein
the physiological data is a physiological signal;
establishing a relationship between the physiological data and the input signal comprises determining a period of periodic portions in the physiological signal, to determine a physiological signal period; and
the plurality of periodic portions in the input signal are identified based on the physiological signal period.

3. The method according to claim 2, further comprising generating electrical signals for an electrode based on correlation of the identified periodic portions of the input signal with the physiological signal.

4. The method according to claim 1, further comprising auto-correlating the input signal to identify the periodic portions in the input signal.

5. The method according to claim 1, wherein calculating a frequency spectrum of at least a portion of the first input signal comprises calculating a frequency spectrum of an individual pulse in the input signal.

6. The method according to claim 5, wherein identifying a demodulation frequency within the frequency spectrum comprises identifying a frequency peak in the frequency spectrum, wherein the demodulation frequency is the frequency peak.

7. The method according to claim 1, further comprising outputting the identified periodic portions of the input signal to an external device, wherein the external device is at least one of a display device or a storage module.

8. The method according to claim 1, wherein the input signal is indicative of activity in an autonomic nerve of a subject.

9. A nerve activity monitoring system comprising:
a communication interface arranged to receive an input signal indicative of detection of electrical activity in a nerve of a subject and arranged to receive physiological data indicative of physiological activity in the subject;
a spectrum module arranged to calculate a frequency spectrum of at least a portion of the input signal;
a frequency identification module arranged to identify a demodulation frequency within the frequency spectrum;
a demodulator module arranged to demodulate at least two periodic portions of the input signal based on the demodulation frequency, to generate at least two demodulated signal portions; and
an averaging module arranged to average the at least two demodulated signal portions, to generate an averaged signal; and
an output module arranged to:
establish a relationship between the physiological data and the input signal;
identify a plurality of periodic portions in the input signal based on the relationship between the physiological data and the input signal; and
output the periodic portions identified by averaging the plurality of periodic portions of the input signal together, to generate an averaged output signal.

10. The system according to claim 9, wherein the physiological data is a physiological signal, and establishing a relationship between the physiological data and the input signal comprises determining a period of periodic portions in the physiological signal, to determine a physiological signal period;
wherein the plurality of periodic portions in the input signal are identified based on the physiological signal period.

11. The system according to claim 9, wherein identifying a demodulation frequency within the frequency spectrum comprises identifying a frequency peak in the frequency spectrum, wherein the demodulation frequency is the frequency peak.

12. The system according to claim 9, further comprising a correlation module arrange to correlate the identified periodic portions of the input signal with the physiological signal, wherein the communication interface is arranged to output electrical signals for an electrode based on the correlation of the identified periodic portions of the input signal with the physiological signal.

13. The system according to claim 9, wherein the identified periodic portions of the input signal are output to an external device, and wherein the external device is at least one of a display device or a storage module.

14. A nerve activity monitoring system comprising:
a communication interface arranged to receive an input signal indicative of detection of electrical activity in a nerve of a subject and arranged to receive physiological signal indicative of physiological activity in the subject;
a frequency identification module arranged to identify a frequency peak by:
correlating the frequency spectrum with the physiological signal; and
identifying a frequency associated with a frequency peak with the highest correlation with the physiological signal; and
an output module arranged to:
establish a relationship between the physiological signal and the input signal by determining a period of periodic portions in the physiological signal, to determine a physiological signal period;

identify a plurality of periodic portions in the input signal based on the relationship between the physiological signal and the input signal, wherein the plurality of periodic portions in the input signal are identified based on the physiological signal period; and output the periodic portions identified.

\* \* \* \* \*